United States Patent [19]

Scapini et al.

[11] 4,246,407
[45] Jan. 20, 1981

[54] METHOD OF MAKING A FOMINOBEN/THEOPHYLLINE COMPLEX

[75] Inventors: Giancarlo Scapini, Bologna; Armando Raimondi, Anagni; Placido Poidomani, Rome, all of Italy

[73] Assignee: Farmaceutici Geymonat Sud S.p.A., Anagni, Italy

[21] Appl. No.: 64,709

[22] Filed: Aug. 8, 1979

Related U.S. Application Data

[62] Division of Ser. No. 19,022, Mar. 8, 1979, Pat. No. 4,197,300.

[30] Foreign Application Priority Data

Mar. 13, 1978 [IT] Italy .............................. 67542 A/78

[51] Int. Cl.³ .......................................... C07D 413/02
[52] U.S. Cl. ................................................. 544/118
[58] Field of Search ................................ 544/165, 118

[56] References Cited

PUBLICATIONS

Farbenind, Chem. Abstracts, vol. 37 (1937) p. 418⁷.

Primary Examiner—Alan L. Rotman
Assistant Examiner—R. W. Ramsuer

Attorney, Agent, or Firm—Sughrue, Rothwell, Mion, Zinn and Macpeak

[57] ABSTRACT

Fominoben/theophylline complex is disclosed having the formula:

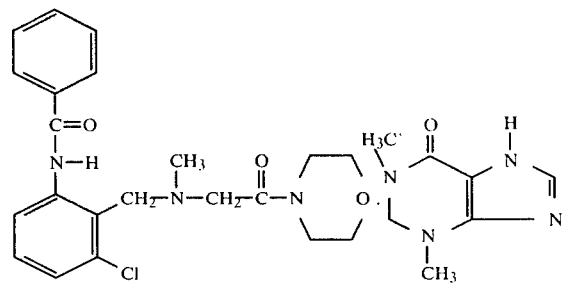

In pharmaceutical oral preparations (dragees or syrup) the complex is usable in dosages corresponding to those of Fominoben hydrochloride, without exhibiting, however, a bitter nauseating taste.

The complex is prepared by refluxing a solution of Fominoben hydrochloride and theophylline sodium salt in equimolar proportions in an alcoholic solvent while at the same time dehydrating the reflux stream.

7 Claims, 1 Drawing Figure

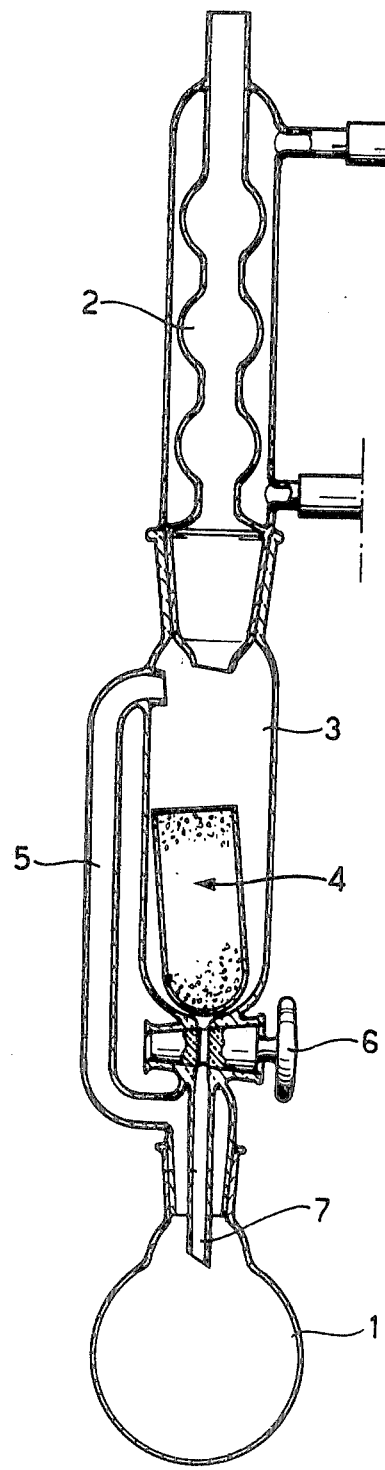

METHOD OF MAKING A FOMINOBEN/THEOPHYLLINE COMPLEX

This is a division of application Ser. No. 19,022, filed Mar. 8, 1979, now U.S. Pat. No. 4,197,300.

FIELD OF THE INVENTION

A drug known as Fominoben, or PB59, or else Nolepan (R.T.M.) was relatively recently introduced commercially, which may chemically be defined as 3'-chloro-2'-{N-methyl-N-[(morpholinocarbonyl)methyl]-aminoethyl}-benzanilide and is used in its soluble form of hydrochloride (Drug of Today, Vol. IX, No. 7, 1973, pages 287–292; Arnheim, Forsch. 26, 1976, pages 438–441).

Fominoben is available in phials and in dragées for intravenous and oral administration, respectively, and is clinically interesting due to both its benefic influence on pathologic alterations of hematic gas composition, analeptic activity on respiratory centres and anti-tussive effect. In particular, oral administration is recommended in cases of respiratory disturbances originating from chronic tussis with bronchitic syndrone, in cases of bronchial emphysema and in cases of "senile lung". Oral administration is done by means of dragees, which shall be swallowed without masticating because of an extremely bitter, nauseating, persistent taste. This circumstance represents a substantial drawback, particularly in pediatric use wherein administration in the form of a syrup (for example) would be highly desirable.

BACKGROUND OF THE INVENTION

Considering the above, a research work was done by Applicants with the view to depress or eliminate the disagreable organoleptic characteristics of the drug described above without impairing its pharmacologically useful properties. It was thus unexpectedly found that Fominoben may be complexed with theophyllinein equimolar proportion and the obtained complex fully solves the problem. It was known that theophylline has analeptic properties on respiratory activity and is exempt of antagonistic side effects, toxicity and teratogenic effects. However, it is to be noted that in practical dosage of the said complex the amount complexed theophylline is far below the therapeutical doses of theophylline used in the prior art, so that there was no logical reason to complex Fominoben with theophyllin with the view to obtain detectable therapeutical benefits, and still less is was expectable that the complex will no longer exhibit the disagreable organoleptic characteristics of Fominoben.

THE INVENTION

An object of this invention resides in a Fominoben/-Theophylline complex corresponding to the structural formula:

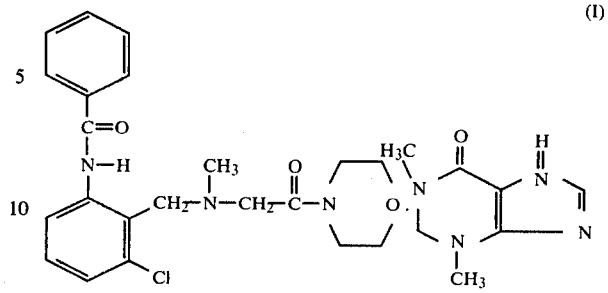

wherein the two partners are in 1:1 molar proportion. Materially, the complex is a white, non-hygroscopic, easily preservable powder.

At 20° C. and in neutral medium (pH=7) the complex is slightly only soluble in water and in most organic (even polar) solvents. The solubility is appreciable in dimethylsulfoxide; however, this polar, potentially basic solvent exhibiting a high chelating power produces a slow dissociation of the complex with consequent crystallisation of theophylline as less soluble component.

In a slightly alkaline (pH 8) or slightly acidic (pH 6) medium the complex dissociates very rapidly into its component principles: Fominoben and theophylline. This circumstance is very favourable in that, once a syrupy neutral (pH=7) suspension of the complex has been administered to a subject, the gastric acidity rapidly liberates Fominoben and converts the latter to hydrochloride, which is absorbed and utilized by subject's organism in the manner typical of conventional Fominoben hydrochloride.

The existence of the complex according to this invention is confirmed by the following circumstances.

(a) Organoleptic characters

The complex is completely exempt of the bitter, nauseating, persistent taste typical of Fominoben.

(b) Behaviour on melting

The behaviours is typical of organic complexes in that the present complex starts softening at about 140° C., forms a first liquid drop at 190°–195° C. and is completely molten (without decomposition) at 230°–235° C. It is to be noted that the melting point of Fominoben in free condition (not hydrochloride) is 121°–123° C., while the melting point of theophylline monohydrate is 270°–274° C. It is also to be noted that an intimate fine mixture (prepared by accurate trituration in a laboratory mortar) of Fominoben and theophylline starts softening at about 200°–210° C. and melts between 220° and 240° C. with decomposition and gas development.

(c) Infrared Spectrum

The I.R. spectrum of the complex in solid form (in KBr tablets) as compared with that of the free base shows absorptions in regions 3050–3150 cm$^{-1}$ and 2300–2750 cm$^{-1}$ which denote intramolecular interactions of the two compounds forming the complex.

(d) Elemental analysis

The percent values of C, H and N calculated for compounds relevant to this invention are as follows:

|  | C% | H% | N% |
| --- | --- | --- | --- |
| Fominoben (free base) | 62,76 | 6,02 | 10,46 |
| Fominoben hydrochloride | 57,53 | 5,75 | 9,59 |
| Theophylline monohydrate | 42,46 | 5,09 | 28,29 |
| Theophylline Na-salt monohydrate | 38,18 | 4,12 | 25,45 |
| Theophylline/Fominoben complex 1:1 | 57,78 | 5,54 | 16,84 |

It will be noted that the complex 1:1 is characterized by a strong variation (as compared with Fominoben and theophylline) of nitrogen percentage. As will be practically shown by way of an Example hereinafter, this variation is indicative of both the termination of the complex-forming reaction and quality of the obtained product.

It is to be understood that the scope of this invention also includes analogues and derivatives of the complex disclosed above as well as anti-tussive preparations comprising said complex, analogues and derivatives as active agent. The invention particularly includes the said preparations in syrup form, having a pH value of substantially 7.

It is also an object of this invention to provide a process for preparing the said complex. The process is essentially characterized by the steps of reflux-heating a solution of Fominoben hydrochloride and theophylline Na-salt monohydrate in liquid alcoholic solvent (mainly a lower alkanol) in equimolar proportions, and at the same time dehydrating the reflux stream. Dehydration is preferably done by means of a dehydrating agent, e.g. anhydrous sodium sulfate. The amount dehydrating agent is proportioned to the reflux flow so as to preferably thoroughly dehydrate the latter, so that the condensate returning to the reaction mass is free of water. The liquid alcoholic solvent preferably consists of isopropanol (b.p. 82.5° C.). Heating under reflux is continued until the reaction is at least substantially complete; in isopropanol, at atmospheric pressure, the reaction typically takes a time of 8–10 hours. Solid sodium chloride forms as by-product removable by filtration; the latter is preferably carried out when the reacted mass is still hot. After NaCl removal, the obtained complex may be recovered by evaporation of the solvent.

The single FIGURE in the appended drawing schematically shows an embodiment of the apparatus which may be used in carrying out the process according to this invention.

The apparatus fundamentally is a known Soxhlet extractor, comprising a glass flask 1 equipped with a reflux-condenser 2 communicating with the flask through a reflux collector 3. A dehydrating cartridge 4 is placed in the collector 3 right below the condenser 2, the cartridge comprising a sachet of filter paper filled with the necessary amount of anhydrous sodium sulfate. Vapours evolving in the flask in operation are conveyed to the top of the collector 3 through a by-pass tube 5. The condensate dripping from the condenser 2 impinges upon the dehydrating cartridge 4, and the dehydrated condensate returns to flask 1 from the bottom of the collector 3 through a cock 6 and a downcomer tube 7. The condenser 2 is cooled by circulation of tap water.

EXAMPLE

The flask 1 of the apparatus described above is charged with 500 ml of substantially anhydrous isopropanol, 17.54 grams (0.04 mols) of Fominoben hydrochloride and 8.81 grams (0.04 mols) theophylline Na-salt monohydrate. Reflux heating is applied and continued for 10 hours, whereupon the reacted hot mass is filtered through a filter paper and the filtrate is collected. The flask is washed twice with boiling isopropanol (50 ml each time) and the washings are united with the filtrate. This solution is evaporated to dryness, the solid residue sticking to the internal surface of the evaporation vessel is taken-up with cold absolute ethanol, used in four portions of 25 ml each, and the obtained suspension is filtered on Buchner filter to recover the solid product therefrom. The product collected on the filter is washed twice (10 ml each time) of the same ethanol used before and dried in a thermostatically controlled oven at 90° C. The dry product is finely ground and dried again at 90° C. In this way 20 grams pure product are obtained, with a yield of 85% of the theoretical. The product perceptibly softens at 150° C., forms a first liquid drop at 193° C. and completely melts at 232° C.

Analysis for $C_{28}H_{32}ClN_7O$: calculated % C 57.78; H 5.54; N 16.84. found % C 58.43; H 5.50; N 16.50.

The product has practically no taste. Its is easily compoundable into tablets and syrups, provided that pH value of the syrup containing the dispersed product is at least substantially 7. It may be noticed that by acidifying the syrup with HCl to a pH value below 6, the product undergoes cleavage into Fominoben hydrochloride and theophylline, and the syrup exhibits the bitter nauseating taste characteristic of Fominoben. A similar cleavage is produced at pH exceeding 8, by addition of caustic soda, yielding Fominoben and theophylline sodium salt.

PHARMACEUTICAL PREPARATIONS

It is advisable to notice at this point that Fominoben-HCl is typically used in the form of dragées containing various unit-dosages of the drug. For adults, in case of respiratory disturbances such as chronic bronchitis, pulmonary emphysema, etc., the unit-dosis is about 160 mg, and two (max. three) dragées daily are used. For pediatric use as anti-tussive, the unit dose varies from about 20 mg to about 40 mg, depending upon the age; typically, 1.33–1.66 mg/kg body weight are administered daily to children aged 28–40 months, whereas 5.4–6.8 mg/kg body weight may be administered daily to children aged 3.5 to 5 years.

These circumstances provide (at least at present) a guideline in the formulation and use of the complex according to this invention.

Dragées or tablets:

A recommended composition for dragées is the following:

Fominoben/Theophylline complex: 212.5 parts by weight
Lactose: 77.5 parts by weight
Starch: 100.0 parts by weight
Magnesium stearate: 10.0 parts by weight from which dragées are formed containing each a unit-dose of 212.5 mg complex, corresponding to 160 mg Fominoben-HCl.

Syrups

A syrup may be prepared in the following manner.

133 grams saccharose in 67 ml water are heated to boil and the obtained sugar solution (200 g) is left to cool.

At the other hand, 2.4 g methyl p-hydroxybenzoate and 0.6 g propyl p-hydroxybenzoate are dissolved in 800 ml boiling water and the obtained solution is cooled to room temperature, whereupon 20 g dragant gum are added and left to swell over a night. The obtained dispersion is strained through a 100 mesh sieve and placed into a high-speed mixer (emulsifier). The mixer is switched-in, and the gum dispersion therein is additioned with 100 g glycerol, 700 g sorbitol (70% strength solution) and the 200 g sugar solution mentioned hereinbefore. The pH value of the emulsion being worked is corrected to 7 by adding thereto at first NaOH 1 N (grobe adjustment) and subsequently NaOH 0.1 N (fine adjustment). At this point 21.2 g Fominoben/theophylline complex are added, pH value is checked again and, if necessary, re-adjusted by addition of NaOH 0.1 N, whereupon the resulting emulsified suspension is additioned with 25 g extra-fluid licorice juice and 10 g extra-fluid *Thymum Serpyllum* essence. The pH value is checked once again and adjusted, if necessary, to 7 by addition of NaOH 0.1 N, whereupon distilled water is added to make a total volume of 2,000 ml.

The syrup obtained in this manner contains, in each 100 ml, 1.06 grams Fominoben/theophylline complex equivalent to 0.800 grams Fominoben-HCl. The syrup may be administered by means of a teaspoon of 5 g capacity corresponding to 50.3 mg complex, corresponding on its turn to 40 mg Forminoben-HCl. A half-dose mark may advantageously be provided on the teaspoon for administration corresponding to 20 mg Fominoben-HCl.

We claim:

1. Process for preparing a Fominoben/theophylline complex having the formula:

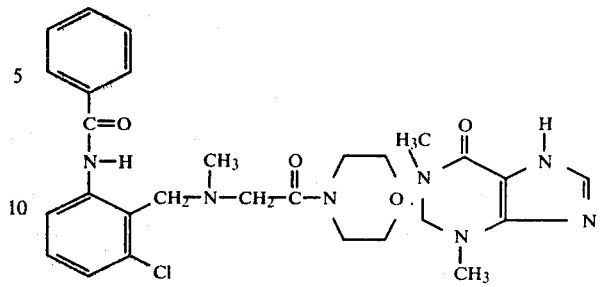

comprising the steps of reflux-heating a solution of Fominoben hydrochloride and theophylline sodium salt in equimolar proportion in a liquid alcoholic solvent, at the same time dehydrating the reflux stream on its return path to the reaction mass, and recovering the said complex.

2. Process as claimed in claim 1, wherein the solvent is a lower alkanol.

3. Process as claimed in claim 2, wherein the solvent is isopropanol.

4. Process as claimed in claim 1, wherein the reflux stream is dehydrated by means of a dehydrating agent.

5. Process as claimed in claim 4, wherein the dehydrating agent is anhydrous sodium sulfate.

6. Process as claimed in claim 1, wherein the recovery procedure of the complex comprises separating from the reaction mass a solid by-product consisting of sodium chloride and recovering the complex from the liquid phase by evaporation of the solvent.

7. Process as claimed in claim 6, wherein the solid sodium chloride is separated by filtering the reaction mass in its still hot condition.

* * * * *